(12) United States Patent
Berguiga et al.

(10) Patent No.: US 8,610,897 B2
(45) Date of Patent: Dec. 17, 2013

(54) HIGH-RESOLUTION SURFACE PLASMON MICROSCOPE WITH HETERODYNE INTERFEROMETRY IN RADIAL POLARIZATION MODE

(75) Inventors: Lofti Berguiga, Lyons (FR); Francoise Argoul, Lyons (FR)

(73) Assignees: Ecole Normale Superieure de Lyon, Lyon Cedex (FR); Centre National de la Recherche Scientifique, Paris Cedex (FR)

(*) Notice: Subject to any disclaimer, the term of this patent is extended or adjusted under 35 U.S.C. 154(b) by 533 days.

(21) Appl. No.: 12/747,266

(22) PCT Filed: Dec. 11, 2008

(86) PCT No.: PCT/FR2008/052279
§ 371 (c)(1),
(2), (4) Date: Sep. 1, 2010

(87) PCT Pub. No.: WO2009/080998
PCT Pub. Date: Jul. 2, 2009

(65) Prior Publication Data
US 2010/0328674 A1 Dec. 30, 2010

(30) Foreign Application Priority Data
Dec. 11, 2007 (FR) ...................................... 07 59716

(51) Int. Cl.
*G01B 9/02* (2006.01)
(52) U.S. Cl.
USPC ........................................................ 356/487
(58) Field of Classification Search
USPC ........................................................ 356/487
See application file for complete search history.

(56) References Cited

U.S. PATENT DOCUMENTS 5,028,136 A    7/1991  Murarka et al.
5,229,833 A *  7/1993  Stewart .......................... 356/364
(Continued)

FOREIGN PATENT DOCUMENTS

FR    2 924 805 A1    6/2009
JP    2003-83886      3/2003

OTHER PUBLICATIONS

L. Berguiga et al., "High-resolution surface-plasmon imaging in air and in water: V(z) curve and operating conditions", Optics Letters, Mar. 1, 2007, vol. 32, No. 5, p. 509-511.

(Continued)

*Primary Examiner* — Tara S Pajoohi Gomez
*Assistant Examiner* — Jonathan Cook
(74) *Attorney, Agent, or Firm* — Clark & Brody

(57) ABSTRACT

The present invention relates to a high-resolution scanning surface-plasmon microscope including a source (LG) of coherent light and a medium for coupling and confining a surface plasmon including an objective (O, $O_M$) with a large numerical aperture, immersion oil ($H_i$), and a glass cover slip ($G_S$). A metal layer ($M_S$) covers a surface of the glass cover slip ($G_S$). The microscope also includes a heterodyne-mode Twyman-Green interferometer placed between the light source and means ($PL_1$, $PL_2$, EC) for scanning the metal layer using a light beam and means (PD) for detecting the beam from the interferometer connected to processing means (S, F, $D_{Tec}$, COMP) for forming an image from that beam. According to the invention, at least one polarization converter (CP) for converting the light beams (L) emitted by the light source (LG) from linear polarization to radial polarization is disposed between the light source and the interferometer.

8 Claims, 6 Drawing Sheets

(56) References Cited

U.S. PATENT DOCUMENTS

| | | | |
|---|---|---|---|
| 5,623,339 A * | 4/1997 | Wickramasinghe et al. | 356/501 |
| 6,970,249 B1 * | 11/2005 | Lipson et al. | 356/445 |
| 2004/0100636 A1 * | 5/2004 | Somekh et al. | 356/497 |
| 2007/0070357 A1 * | 3/2007 | Aiyer | 356/485 |

OTHER PUBLICATIONS

K. Watanabe et al., "Optimized measurement probe of the localized surface plasmon microscope by using radially polarized illumination", Applied Optics, Aug. 1, 2007, vol. 46, No. 22, p. 4985-4990.

M. Somekh et al., "Optical V(z) for high-resolution 2π surface plasmon microscopy", Optics Letters, Jun. 1, 2000, vol. 25, No. 11, p. 823-825.

M. Somekh et al., "High-resolution scanning surface-plasmon microscopy", Applied Optics, Dec. 1, 2000, vol. 39, No. 34, p. 6279-6287.

E. Hecht, "Optics—second edition", 1987, Addison-Wesley Publishing Company, Inc., XP002533179, ISBN: 0-201-11611-1, p. 385-386.

* cited by examiner

HIGH-RESOLUTION SURFACE PLASMON MICROSCOPE WITH HETERODYNE INTERFEROMETRY IN RADIAL POLARIZATION MODE

TECHNICAL FIELD OF THE INVENTION

The present invention relates to a high-resolution surface-plasmon microscope including a heterodyne interferometer and using radial polarization of the beam for generating the surface plasmon.

The technical field of the invention is that of designing imaging systems for detecting small variations of refractive index in an observation medium and/or dielectric objects of the order of a few nanometers that do not necessarily have remarkable optical properties (fluorescence, luminescence, localized plasmon resonance or Raman resonance) and are located near a surface and immersed in any medium with a refractive index less than 1.5 and notably in air or an aqueous medium.

PRIOR ART

A surface plasmon is a surface electromagnetic wave that propagates in an interface between a metal and an observation dielectric medium.

The creation of this effect, i.e. the excitation of the surface plasmon, requires particular optical coupling conditions. It requires a coupling medium and light incident on the interface between the metal and the dielectric medium at a particular angle that is usually referred to as the plasmon resonance angle $\theta_p$.

Apart from the resonance properties of the surface plasmon, the angle $\theta_p$ (in other words the coupling condition) is very sensitive to even the slightest modifications of the optical properties at the interface between the metal and the dielectric medium. This sensitivity means that the surface plasmon can be used to produce images of objects of very small size situated at the interface between the metal and the dielectric medium, said objects modifying the optical properties of the surface plasmon at that interface to enable contrast to be achieved between the object and its medium.

Because the surface plasmon is an evanescent wave, it excludes volume effects within the observation medium.

The theory of plasmon excitation in surface-plasmon microscopy is very often illustrated in the literature by referring to the so-called Kretschmann-Raether configuration. This provides for depositing a metal layer with a thickness of the order of 50 nanometers (nm) onto a face of a glass prism in contact with a dielectric medium such as air. If a high-intensity beam of light passes through the prism and encounters the metal layer at the angle of incidence $\theta_p$, then a surface plasmon is created in the metal and the resulting evanescent wave is confined within a few hundred nanometers of the interface between the metal and the dielectric medium.

Of all the waves reaching the surface, only those that have an angle of incidence sufficiently close to the plasmon resonance angle $\theta_p$ (typically to within less than two degrees) excite the surface plasmon and contribute to surface-plasmon imaging. At present surface plasmons are essentially used as chemical and/or biological sensors and systems based on the Kretschmann configuration are commercially available. However, the resolution of such systems, being limited by the lateral propagation of the plasmon, is relatively low, of the order of only a few tens of micrometers (μm) at visible wavelengths.

Over about a decade a small number of fundamental research groups have developed a generation of surface-plasmon microscopes with a resolution that is no longer limited by lateral propagation of the plasmon, as before, but only by diffraction.

Those microscopes all employ the common concept of using an objective of high numerical aperture and high magnification to focus a laser beam onto a surface that features a metal (gold, silver, copper, aluminum, etc.) layer that is a few tens of nanometers thick. This both excites and confines the thin film surface plasmon.

Those techniques nevertheless differ firstly in the illumination profile at the entry of the objective and secondly in the signal detection mode.

When a beam reaches the entry of the objective of the microscope, only a very fine ring of light contributes to excitation of the surface plasmon. The part of the reflected beam that contains the information associated with the surface plasmon is very fine and is buried in the rest of the light beam. Without special processing of the beam, imaging would be virtually impossible.

In some publications, notably in Japanese patent application JP 2003083886, illumination and detection are based on spatial filtering of the light rays at the entry of the objective that contribute to plasmon excitation and eliminating those that do not contribute to it.

Other publications, such as U.S. Pat. No. 6,970,249 B1 or better still the papers by M. G. Somekh, S. G. Liu, T. S. Velinov, and C. W. See, "Optical V(z) for high-resolution plasmon microscopy", Optics Letters 25, 823 (2000) and "High-resolution scanning surface-plasmon microscopy", Applied Optics 39, 6279 (2000), propose the use of an interferometer. Although more costly, that method achieves greatly improved sensitivity.

The paper by Somekh et al. proposes a microscopy device as shown in FIGS. 1B and 2A that makes it possible to measure the phase but does not filter the light rays that do not contribute to plasmon excitation by eliminating the part devoid of interest. The coupling of these two technical aspects has the advantage of unrivalled resolution and sensitivity compared to other techniques known at present.

Nevertheless, in this particular implementation, as shown in FIG. 2B, which represents the distribution of the intensity of the laser beam in the rear focal plane of the objective after backscattering and passing through the objective again, there are seen two crescent-shaped rings that correspond to the area of the initial beam that contributed to excitation of the surface plasmon. The area of the rays concerned has a special orientation, namely that of the direction of polarization of the light at the entry to the objective. In the device proposed by Somekh, no ray contributes to excitation of the surface plasmon in the orthogonal direction (i.e. the vertical direction passing through 0 in FIG. 2B) and only a fraction of the incident light energy participates in the excitation of the surface plasmon.

Finally, document US 2004/0100636 discloses the possibility of obtaining better image resolution with a radially-polarized excitation beam. However, the above document does not disclose any example of a microscope structure using that principle or any measurement effected with radial polarization that validates the measurement principle referred to.

One object of the present invention is to provide a high-resolution surface-plasmon microscope that has improved resolution and sensitivity compared to existing surface-plasmon microscopes.

Another object of the invention is to provide a surface-plasmon microscope enabling observation of molecules and particles in aqueous dielectric media, and notably in biological liquids.

The invention aims in particular to provide a high-resolution surface-plasmon microscope for detecting and viewing objects of very small size, of the order of one nanometer, such as biological molecules, for example, without using chemical, optical, or radioactive markers of those objects.

A final object of the invention is to provide a surface-plasmon microscope that is simple to implement and to use.

STATEMENT OF THE INVENTION

The stated objectives are achieved by the present invention by means of a high-resolution scanning surface-plasmon microscope essentially including:

a) a source of coherent light;
b) a medium for coupling and confining a surface plasmon including an objective with a large numerical aperture, immersion oil, and a glass cover slip;
c) a metal layer covering a surface of the glass cover slip of the coupling medium that is not in contact with the immersion oil thereof, the metal layer being adapted to be brought into contact with an observation medium containing a sample to be observed and to emit a surface plasmon generated by excitation of at least one light beam coming from the light source;
d) a heterodyne-mode Twyman-Green interferometer adapted to split a light beam emitted by the light source into at least one reference beam and at least one measurement beam directed toward the coupling medium and the metal layer to generate a surface plasmon, the interferometer being positioned between the light source and the objective of the coupling medium to form an interferometric beam between the reference beam and the measurement beam after reflection of each of them by a mirror and by the metal layer, respectively;
e) means for scanning the metal layer with the measurement light beam;
f) means for detecting the interferometric beam from the interferometer; and
g) processing means for forming an image from the interferometric beam.

The microscope of the invention is characterized in that it includes, disposed between the light source and the interferometer, at least one polarization converter for converting from linear polarization to radial polarization the light beams emitted by the light source, and enabling detection of dielectric and metal objects with a diameter less than 10 nm without marking.

Thus the microscope of the invention differs from the prior art in that it enables conversion of the beam for generating the surface plasmon to be converted to radial polarization.

The introduction of such a facility for illuminating the interface between the metal layer and the observation dielectric medium with a radially-polarized beam provides a significant advance over the prior art because, as described below, it improves the resolution of the images obtained by a factor of 3 and the sensitivity by a factor of 4.

The invention also provides a method of heterodyne interferometer high-resolution surface-plasmon microscopy developed for use in the microscope of the invention.

This method comprises the steps of:

using a measurement light beam produced by a coherent light beam introduced into a heterodyne-mode Twyman-Green interferometer to illuminate a sample to be imaged that is disposed on a metal layer coating a glass cover slip of a medium for coupling and confining a surface plasmon also including an objective with a large numerical aperture and immersion oil;

scanning the surface of the metal layer with the measurement beam guided by scanning means;

detecting an interferometric light beam at the exit from said Twyman-Green interferometer by detection means; and processing said interferometric beam and forming an image of the surface plasmon emitted by the metal surface in contact with the sample to be imaged by processing and image-forming means.

According to the invention, this method is characterized in that the beam of coherent light is radially polarized by a polarization converter before it enters the interferometer so as to illuminate the sample to be imaged on the metal layer of the coupling medium with a measurement beam that is radially symmetrical relative to its propagation axis.

The polarization conversion induced by the method of the invention is used in an entirely novel and advantageous variant in the field of high-resolution surface-plasmon microscopy, namely differential mode imaging, which makes it possible to further improve the contrast and the dynamic range of the images obtained.

In this advantageous variant of the method of the invention, the beam of coherent light is alternately polarized by the polarization converter in pure p mode (radial polarization) and in pure s mode (azimuth polarization) and the surface of the metal layer is scanned linearly, alternately and synchronously with the alternating polarization of the beam of coherent light by the measurement beam polarized alternately in pure p mode and in pure s mode.

DESCRIPTION OF THE DRAWINGS

Other features and advantages of the microscope of the invention emerge more clearly from the following detailed description with reference to the appended drawings, in which.

DETAILED DESCRIPTION OF EMBODIMENTS OF THE INVENTION

The present invention proposes a high-resolution scanning surface-plasmon microscope utilizing the principle of the so-called V(z) effect whereby the response V of the microscope varies as a function of the defocusing distance z relative to the interface between the metal layer and the observation dielectric medium of the microscope.

The first conclusive experiments on using this V(z) effect principle are described in particular in the above-mentioned paper by M. G. Somekh, S. G. Liu, T. S. Velinov, and C. W. See, "Optical V(z) for high-resolution 2 p plasmon microscopy", Optics Letters 25, 823, (2000), and "High-resolution scanning surface-plasmon microscopy", Applied Optics 39, 6279 (2000) for measurements in air and in the paper by L. Berguiga, S. Zhang, J. Elezgaray, and F. Argoul "High-resolution surface-plasmon imaging in air and in liquids: V(z) curve and operating conditions", Optics Letters 32, 509 (2007), for measurements in water.

The essential elements of the above experiments are summarized below with reference to FIGS. 1A to 2B and explain the V(z) effect in high-resolution surface-plasmon microscopy and consequently in the microscope of the present invention, which is more particularly described with reference to FIGS. 3A to 6.

Figure 1A:
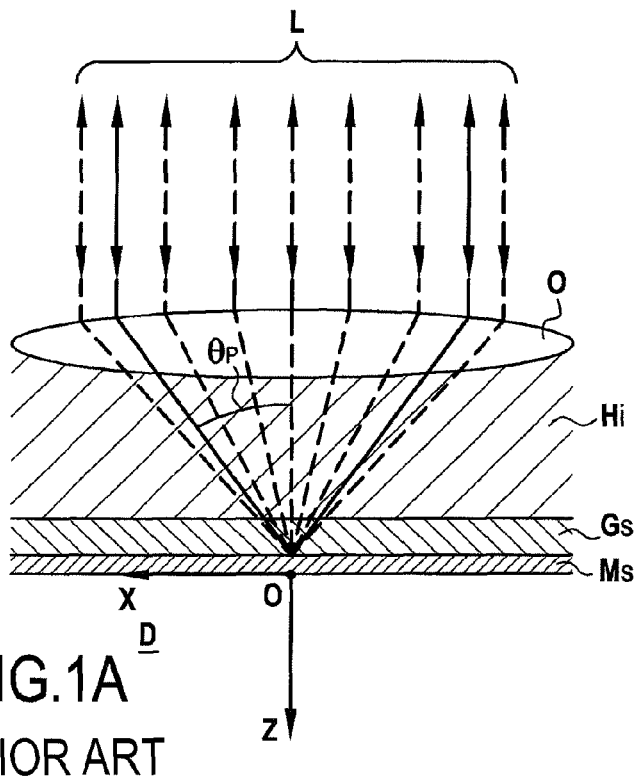
FIG. 1A represents the principle of surface plasmon excitation and confinement in a prior art microscope with a focused light beam at the interface between the metal and the dielectric medium.
Figure 1B:
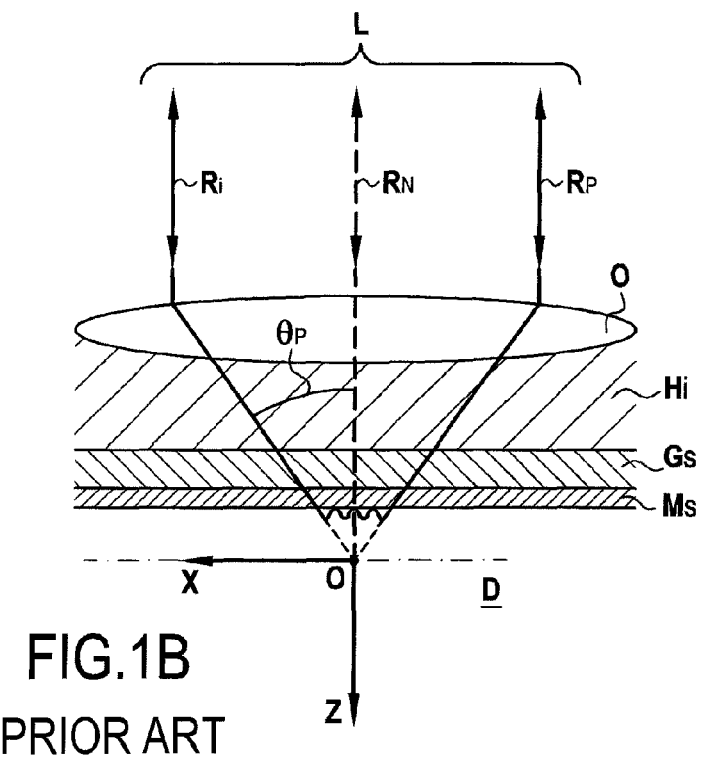
FIG. 1B represents the principle of surface plasmon excitation and confinement in a prior art microscope with a defocused light beam at the interface between the metal and the dielectric medium.
Figure 1C:
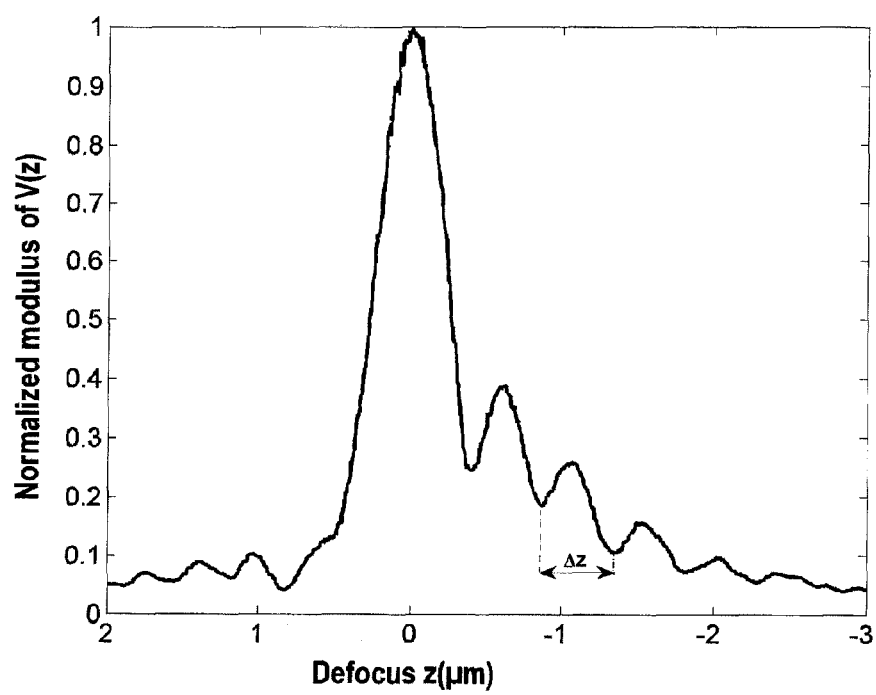
FIG. 1C represents an experimental V(z) curve obtained in water with a prior art linear polarization surface-plasmon microscope.

Referring to FIGS. 1A and 1B, the principle of surface plasmon excitation in high-resolution surface-plasmon microscopy is analogous to the so-called Kretschmann configuration. It uses a coupling medium that replaces the glass prism of the Kretschmann configuration. This coupling medium consists of an objective O with a high numerical aperture, typically at least 1.2 NA, with the surface of one of its diopters immersed in an immersion oil $H_i$ that is itself in contact with a first face of a glass cover slip G. The free face of the glass cover slip $G_S$ (i.e. the face not in contact with the oil) is covered with an approximately 45 nm thick layer $M_S$ of metal, for example of gold or silver.

In contact with the metal layer and extending in the direction of the axis Z in FIG. 1A is an analysis or observation dielectric medium D in which objects to be observed are immersed. This analysis medium D can be air, water, an aqueous solution, or more generally any dielectric medium having a refractive index less than or equal to 1.5.

A light beam L such as a laser beam represented by the double-headed arrows in FIGS. 1A and 1B is directed toward the metal layer $M_S$ through the coupling medium. Of all the rays reaching the metal layer $M_S$ and the interface thereof with the dielectric medium D, only those that are reflected at the metal layer with an angle of incidence close to the plasmon resonance angle $\theta_p$ excite the surface plasmon represented by the solid line rays in FIG. 1A at the interface between the metal layer $M_S$ and the dielectric observation medium D.

As represented in FIG. 1A, when this light beam L is focused in the plane of the interface between the metal layer $M_S$ and the dielectric medium D, all the light rays of the incident beam are reflected and reach a detector (not shown) placed at infinity. To utilize the surface plasmon and to obtain an image it is then necessary to eliminate all the reflected rays that do not contribute to generating the plasmon, i.e. all the beams represented in dashed line in FIG. 1A.

To circumvent this problem, by means of defocusing the plane of the objective O to the rear of the metal surface $M_S$ by geometrical optical construction, as shown in FIG. 1B, none of the reflected beams that do not pass through the point O reach the photodetector placed at infinity. Here only the beam at normal incidence and the rays that contribute to generating the surface plasmon reach the photodetector.

In FIG. 1B, the defocusing of the focal plane of the objective O to the rear of the metal surface $M_s$ to be observed enables the surface plasmon excited by the ray $R_i$ to propagate and to re-emit rays with an angle $\theta_p$ throughout its propagation at the interface, and only the ray that passes through O, i.e. the ray $R_p$ propagates in the direction of the photodetector.

The phase of this ray lags relative to the ray $R_n$, which is the normal ray reflected on the axis of the objective. This lag is introduced by the propagation of the surface plasmon inside the focusing spot and has the value $\Delta\Phi = p + 4\pi n_o z (1 - \cos\theta_p)$, where $n_o$ is the refractive index of the coupling medium. It varies with the defocusing distance z along the Z axis in the XOZ system of axes and with the speed of propagation of the surface plasmon. By fixing the defocusing distance z, the phase difference between the rays $R_n$ and $R_p$ is linked only to the coupling condition, in other words to the angle $\theta_p$.

Measuring this phase difference and scanning the surface point by point make it possible to probe local variations of plasmon resonance and thus to visualize local variations of the optical properties at the interface with a resolution commensurate with the size of the focused light spot.

The image is then formed point by point.

Figure 2A:
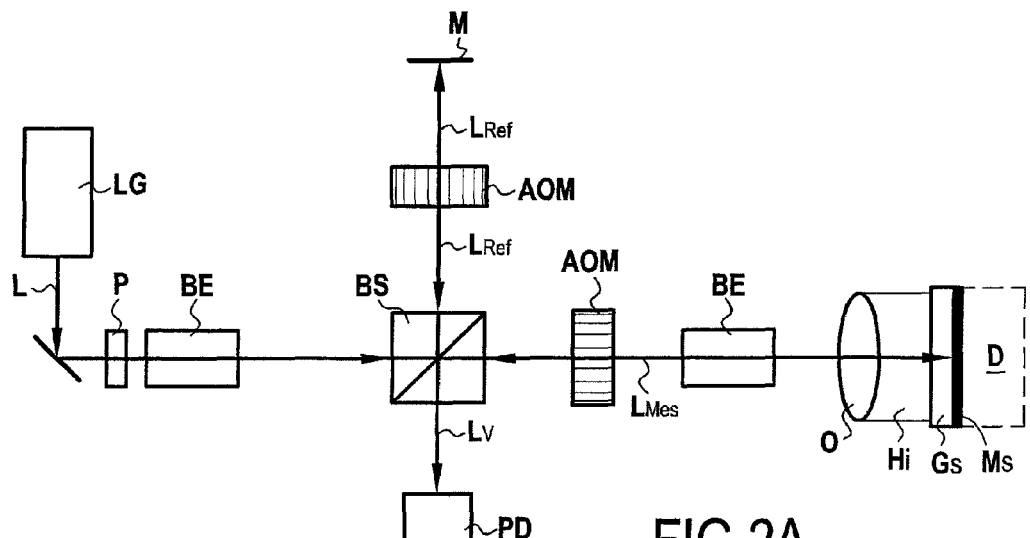
FIG. 2A represents a prior art high-resolution surface-plasmon microscope using excitation and confinement of the surface plasmon in the manner represented in FIG. 1B.

The above technique is used in the microscope proposed in the publication referred to above, a diagram of which is reproduced in FIG. 2A.

As that figure shows, the device includes a laser source LG the beam L from which is divided in two by a beam splitter BS, thus forming an interferometer. After enlargement by a beam enlarger BE one of the two beams passes through a coupling medium comprising an objective O, which enables plasmon excitation by means of its very high numerical aperture and plasmon confinement by means of its high magnification, an immersion oil $H_i$, and a glass cover slip covered on its external surface with a metal (gold or silver) layer $M_S$ in contact with a dielectric observation medium D. The beam reflected by the metal layer $M_S$ passes through the objective O again and is recombined with the other beam that has been reflected by a mirror M. The two beams generate an interference signal with temporal modulation generated by a different shift of the optical frequency in each interferometer arm. The interferometer signal is collected by a photodetector PD and an electronic circuit demodulates the modulated signal.

The signal obtained in this way represents the intensity of one pixel of the image. It is therefore possible by moving the incident beam over the metal surface $M_S$ to scan completely the interface between the metal layer $M_S$ and the observation medium D and reconstitute a complete image.

Figure 2B:
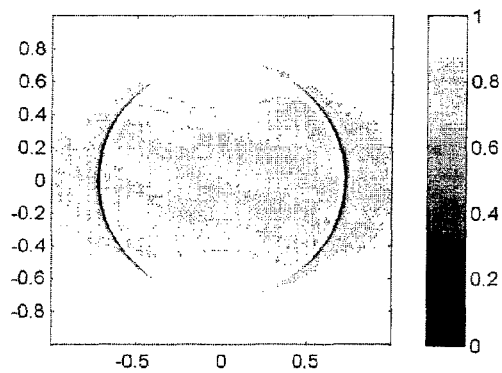
FIG. 2B represents the distribution profile of light reflected by the metal surface generating the surface plasmon at the exit from the objective of the FIG. 2A microscope.
Figure 2C:
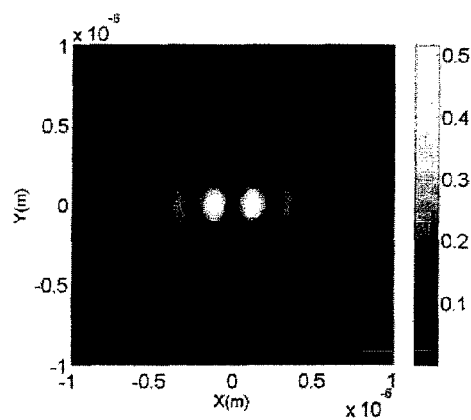
FIG. 2C represents the impulse response of the FIG. 2A microscope with linear polarization by numerical calculation of the distribution of the focused light at an interface between a metal (gold) layer and a dielectric medium formed by water with an objective numerical aperture equal to 1.65.

Nevertheless, as FIG. 2B shows, the distribution of light reflected by the metal surface at the exit from the objective of the microscope is not uniform and only two lateral crescents contribute to generating the surface plasmon. This has the disadvantage of producing a microscope whose impulse response consists of two distinct lobes of light. When observing unique molecules or objects smaller than the beam, when the beam passes over the object each of these lobes passes over the object, thus generating a double image of the object as shown in FIG. 2C, for example.

The present invention makes a significant improvement over the prior art, notably by making it possible to obtain a uniform distribution of light at the exit from the objective of the microscope, of resolution and sensitivity that are greatly improved, as explained below.

Figure 3A:
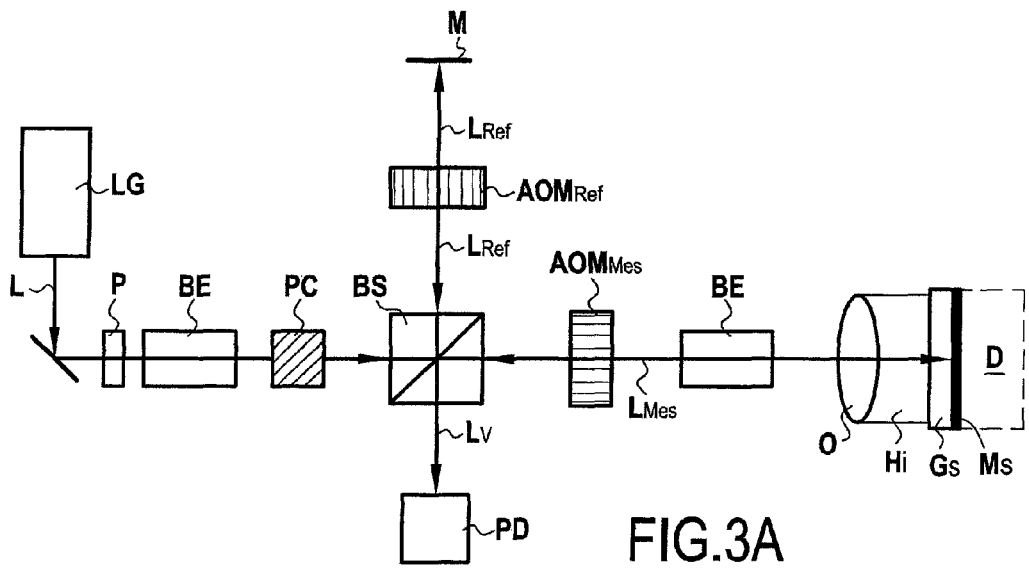
FIG. 3A represents diagrammatically a high-resolution surface-plasmon microscope of the present invention.

A particular embodiment of the microscope of the invention is shown diagrammatically in FIG. 3A in which elements common to the FIG. 2A microscope carry the same references.

In a similar way to the FIG. 2A microscope, the microscope of the invention includes a source LG of coherent light, for example a laser, notably a helium-neon (He—Ne) gas laser.

At the exit from the laser is a polarizer P followed by a beam enlarger BE to enlarge the laser beam L before it enters a heterodyne-mode Twyman-Green interferometer that includes a beam splitter BS to form two laser beams $L_{Ref}$ and $L_{Mes}$ propagating in two distinct arms of the interferometer.

A first or reference laser beam $L_{Ref}$ propagates in a first or reference arm that includes a mirror $M_{Ref}$ for reflecting this first light beam. The second or measurement laser beam $L_{Mes}$ propagates in a second or measurement arm toward a medium for coupling and confining a surface plasmon including an objective O with a high numerical aperture, immersion oil $H_i$ and a glass cover slip $G_S$.

The measurement arm preferably also includes at least one beam enlarger BE between the beam splitter BS and the coupling medium.

Moreover, it is equally preferable and advantageous to provide in each arm of the interferometer at least one acoustical-optical modulator $AOM_{Ref}$, $AOM_{Mes}$, for example consisting of a Bragg cell, adapted to shift the optical frequency of the reference light beam $L_{Ref}$ and the measurement light beam $L_{Mes}$.

The objective O of the coupling medium preferably has a numerical aperture greater than or equal to 1.2 in air and 1.55 in an aqueous solution and a magnification exceeding ×60. These characteristics of the objective O thus ensure good surface plasmon excitation and confinement.

An exterior surface of the glass cover slip $G_S$ of the coupling medium is covered with a metal layer $M_S$ in contact with a dielectric observation medium D containing a sample to be observed and having a refractive index of less than 1.5, for example air or water.

The measurement beam $L_{Mes}$ is thus directed toward the coupling medium and the metal layer $M_S$ to generate a surface plasmon at the interface between the metal layer and the dielectric medium.

The measurement beam $L_{Mes}$ reflected by the metal surface $M_S$ passes through the objective O again and is then recombined with the beam $L_{Ref}$ reflected by the mirror $M_{Ref}$ in the reference arm. The two beams generate an interferometric signal collected by photodetector means PD such as a photomultiplier or a CCD camera, for example, a photon counter or an avalanche photodiode.

This interferometric signal is temporally modulated by shifting the optical frequency of each reflected light beam in each arm of the interferometer.

To demodulate and process this signal, the microscope includes appropriate demodulation electronics and processing means consisting essentially of computer processing and display means for forming an image from the interferometric beam.

According to an essential feature of the invention, the microscope of the invention is distinguished from prior art microscopes and notably from that of Someck et al. in that it includes, between the light source LG and the interferometer, at least one converter CP for converting the laser beam L emitted by the light source LG from linear polarization to radial polarization.

Figure 5:
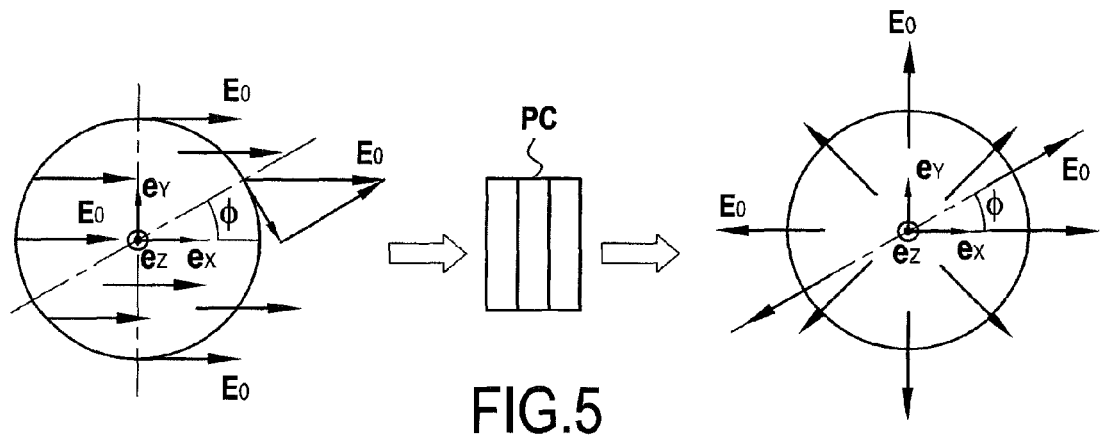
FIG. 5 represents diagrammatically the effect of polarization conversion of the electric field of the light beam used in the microscope of the present invention to generate the surface plasmon.

Converting the laser beam L emitted by the light source LG to radial polarization makes it possible to illuminate the entry of the objective O of the coupling medium with a polarization that has radial symmetry relative to the axis of the beam, as shown in FIG. 5. The polarization converter CP advantageously makes it possible to modify the polarization and thus the orientation of all the electric field vectors $E_o$ relative to the propagation axis of the beam L, with the result that these vectors are all oriented radially relative to the propagation axis in order that the contribution to generating the surface plasmon of the wavefronts incident on the metal surface $M_S$ is uniform and optimal.

Figure 3B:
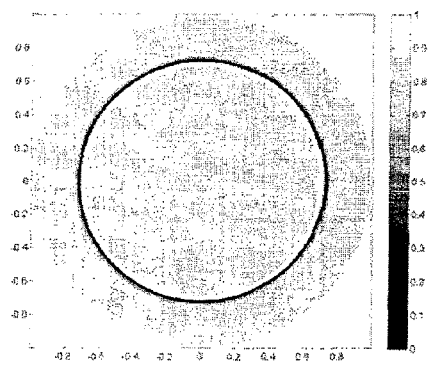
FIG. 3B represents the distribution profile of light reflected by the metal surface generating the surface plasmon at the exit from the objective of the FIG. 3A microscope of the invention.

Accordingly, as FIG. 3B shows, the distribution of reflected light at the exit from the objective is uniform and circular, from which it may be concluded, simply by comparing FIGS. 2B and 3B, that the area of the beam that contributes to plasmon excitation is larger and its area is substantially doubled relative to prior art microscopes.

Figure 3C:
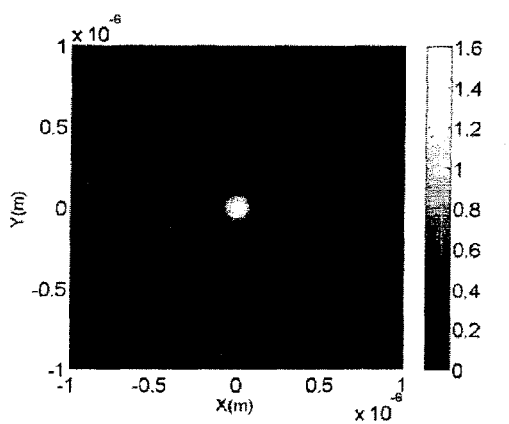
FIG. 3C represents the impulse response of the FIG. 3A microscope with radial polarization by numerical calculation of the distribution of the focused light at an interface between a metal (gold) layer and a dielectric medium formed by water with an objective numerical aperture equal to 1.65.

Furthermore, operation of the surface-plasmon microscope of the invention with radial polarization makes it possible to improve significantly the resolution and the sensitivity of the microscope, as is clearly apparent from FIGS. 2C and 3C, which represent the luminous intensity at the interface calculated for linear polarization and radial polarization, respectively.

As is clear from FIG. 2C, with linear polarization, the luminous intensity distribution at the surface of the focused spot consists of two intense peaks. Consequently, the impulse response of the microscope to an individual nanometer-scale object consists of two bright peaks on respective opposite sides of the object.

In contrast, as is clear from FIG. 3C, with radial polarization, the spot consists of one intense peak that makes it possible firstly to reconcentrate the light beam and secondly to improve the impulse response of the microscope. The intensity of the focused spot obtained with the microscope of the invention is consequently quadrupled.

This experiment shows that the microscope of the invention achieves an improvement of the profile of the optical response because only one peak is obtained instead of two with prior art microscopes and the resolution is tripled, from 600 nm to 200 nm.

Figure 4A:
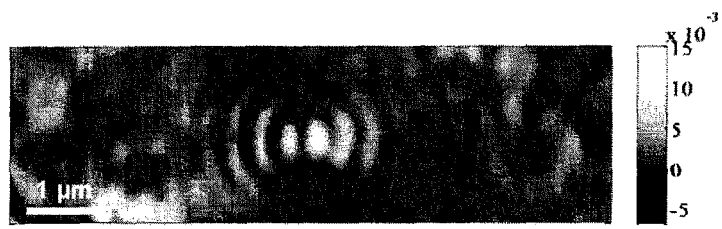
FIGS. 4A and 4B respectively represent the image of a 50 nm diameter latex particle obtained with the prior art microscope shown in FIG. 2A and with the microscope of the invention shown in FIG. 3A.
Figure 4B:
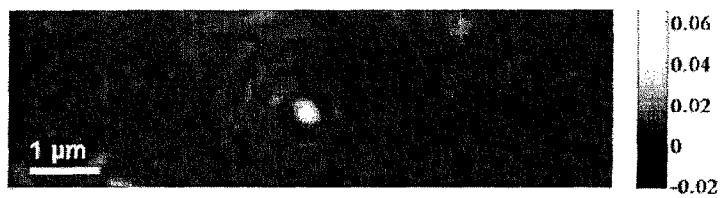

The numerically calculated luminous intensity profiles shown in FIGS. 2C and 3C have been confirmed experimentally by plasmon imaging of 50 nm latex nanoparticles as shown in FIGS. 4A and 4B for linear and radial polarization, respectively.

In order to be able to produce complete images of the surface plasmon, the microscope of the invention includes means for scanning the metal layer with the measurement light beam, notably piezoelectric means for movement in translation of the cover slip and/or the objective of the coupling medium in two mutually orthogonal directions X, Y in the same plane.

To guarantee image contrast, the scanning means of the microscope of the invention include piezoelectric means for moving the objective in translation in a direction Z normal to the plane of each of the surfaces of the glass cover slip of the coupling medium and the metal layer, thus ensuring that the distance of the objective relative to the plate is known.

Figure 6:
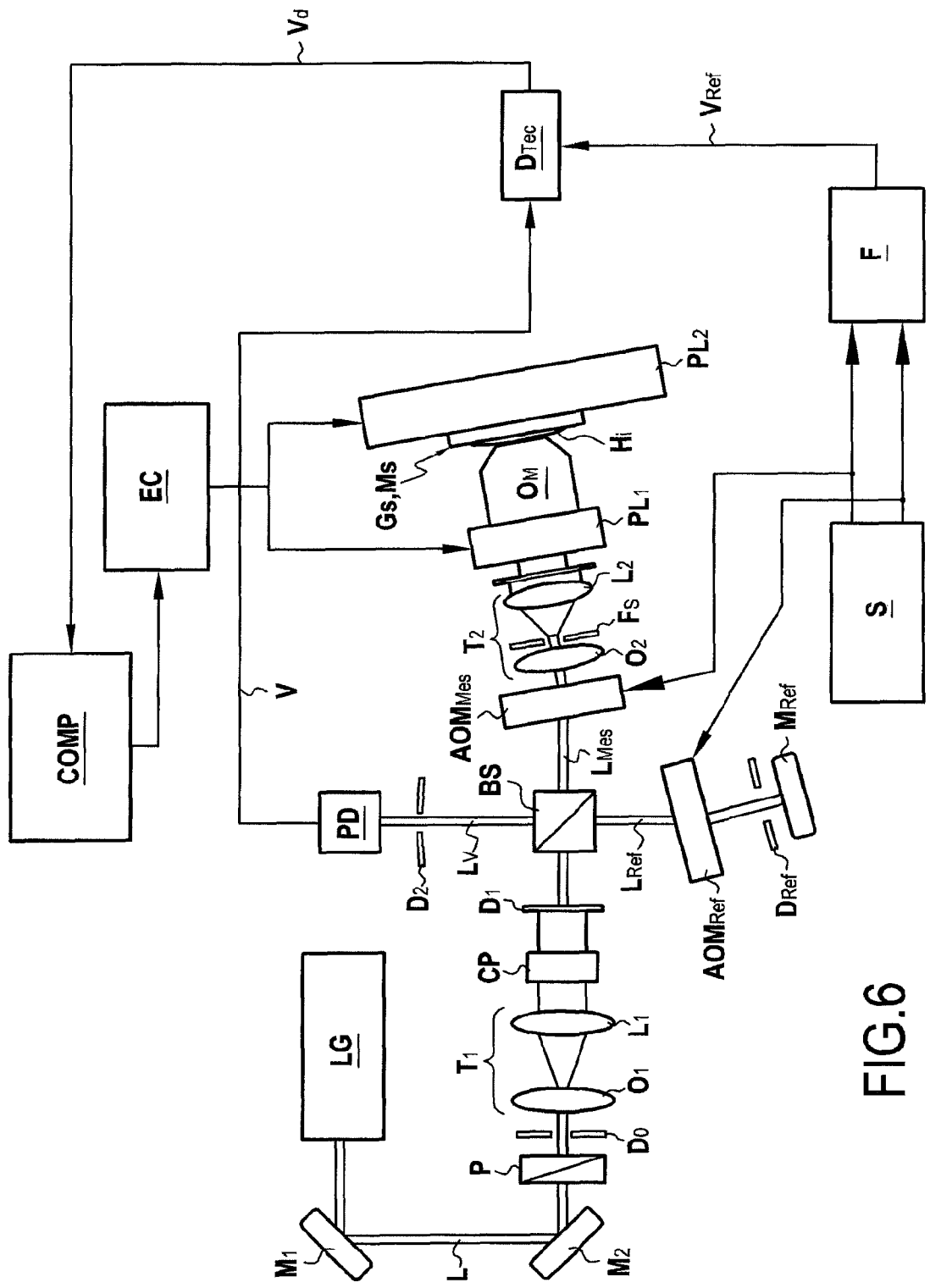
FIG. 6 represents in detail a preferred embodiment of the microscope of the present invention represented diagrammatically in FIG. 3A.

To complete the description of the microscope of the present invention in more detail, FIG. 6 represents in detail a surface-plasmon microscope of a preferred embodiment of the invention.

It includes a light source LG formed by a non-polarized 5 milliwatts (mW), 633 nm He—Ne laser with a coherence length of around 20 centimeters (cm).

This light source LG emits a laser beam L in the direction of two successive mirrors M1 and M2 with an angle of incidence of approximately 45°. These two mirrors M1, M2 enable precise adjustment of the height and the parallelism of the beam L relative to a horizontal plane and an axis that defines the center of all the optical components and notably the axis of symmetry of the focusing objective and the normal incidence direction of the surface of the plate.

The beam L then passes through a polarizer P that polarizes the beam vertically and then a diaphragm D0. The beam L is collimated and enlarged by a first telescope T1 consisting of an objective O1 and a lens L1. Its magnification factor is 2.3. The beam L then passes through a polarization converter CP that converts the uniform distribution of the initial vertical linear polarization into a spatial distribution of the polarization that is radially symmetrical relative to the center of the beam.

Various conversion techniques exist. For example, a system consisting of three layers of liquid crystals has been chosen for the microscope of the invention because it has the advantage of being compact. This technical solution is not exclusive, however, and other types of converter may be employed provided that they enable radial conversion of the excitation laser beam.

At the exit from the converter CP, the laser beam L passes through a diaphragm $D_1$ and then enters a heterodyne-mode Twyman-Green interferometer described below. Placing the converter CP in front of the interferometer is important because it limits optical defects of the wavefront that are subsequently eliminated by the interferometric technique.

The interferometer includes a beam splitter cube BS through which the beam L passes and by which it is divided into two beams $L_{Mes}$, $L_{Ref}$ of equal intensity. The first beam $L_{Mes}$ is not deviated and continues its trajectory in a first arm of the interferometer called the measurement arm (to the right of the cube in the FIG. 6 diagram). The second beam $L_{Ref}$ is deviated 90° relative to the initial beam L. It continues to propagate in a second arm called the reference arm (below the cube in the FIG. 6 diagram).

In the reference arm, the beam enters an acoustical-optical modulator $AOM_{Ref}$ consisting for example of a Bragg cell with an angle of incidence of 6.95 milliradians. An acoustic wave of frequency $O_{Ref}$=75 megahertz (MHz) generated by a synthesizer S and fed to the modulator $AOM_{Ref}$ makes it possible to generate therein a diffraction grating of the beam $L_{Ref}$. Accordingly, on entry of the beam $L_{Ref}$ into the modulator $AOM_{Ref}$, the optical frequency $\omega_{opt}$ of the light is shifted by $+O_{ref}$. The angle of incidence of the beam is then adjusted to the Bragg angle in order to transfer all the luminous intensity into the diffraction order +1. This adjustment makes it possible to obtain 85% of the original intensity, the rest being distributed in decreasing intensity order between the orders 0, −1, 2, −2, etc. This adjustment is made possible by a turntable (not shown) fixed under the modulator $AOM_{Ref}$ and requires a positioning accuracy of better than 0.1 milliradian.

At the exit from the modulator $AOM_{Ref}$, the beam passes through a 2 mm diameter diaphragm $D_{Ref}$ in order to eliminate all the diffracted beams to obtain a beam of order 1 that is shifted in frequency by $O_{Ref}$. This beam then impinges at normal incidence on a reference mirror $M_{Ref}$ of maximum optical quality having a flatness of $\lambda/20$, where $\lambda$ is of course the wavelength of the laser beam L.

The reflected beam $L_{Ref}$ passes through the diaphragm $D_{Ref}$ again and reaches the acoustical-optical modulator $AOM_{Ref}$ with the same Bragg angle as on the outward journey. The beam is diffracted again and shifted by $+O_{Ref}$ at the exit from the acoustical-optical modulator $AOM_{Ref}$. The frequency of this beam is therefore shifted by $2.O_{Ref}$ relative to the initial beam and propagates on the same optical axis as at the exit from the beam splitter cube BS. It passes through the splitter cube again without being deviated and reaches an optical photodetector PD that has a diaphragm $D_2$ at its entry eliminating all diffraction orders other than order 1.

In the measurement arm, the beam $L_{Mes}$ enters an acoustical-optical modulator $AOM_{Mes}$ that is also of the Bragg cell type. An acoustic wave of frequency $O_{Mes}$=75.05 MHz generated by the synthesizer S and fed to the modulator $AOM_{Mes}$ makes it possible to generate therein a diffraction grating of the beam $L_{Mes}$. On entry of the beam $L_{Mes}$ into the modulator $AOM_{Mes}$, the optical frequency $\omega opt$ of the light is shifted by $+\omega_{Mes}$. The angle of incidence of the beam is adjusted to the Bragg angle in order to transfer all the luminous intensity to diffraction order +1. Once again, adjustment of the modulator $AOM_{Mes}$ makes it possible to obtain 85% of the initial intensity, the rest being distributed in decreasing intensity order between the orders 0, −1, 2, −2, etc.

This adjustment is made possible by a turntable fixed under the modulator and not shown in FIG. 6.

Here the principle of selecting the order 1 is different from that of the reference arm, for reasons of overall size and to equalize the lengths of the two arms (measurement and reference).

The diffracted light beams of different orders of the beam $L_{Mes}$ pass through an ×10 magnification objective O2 and a spatial filter FS consisting of a 50 μm diameter hole placed in the image focal plane of the objective O2.

The filter $F_S$ makes it possible firstly to retain only diffraction order 1 and secondly to clean up the beam $L_{Mes}$ by spatial filtering. The divergent beam is collimated by a lens $L_2$ of 100 mm focal length. The telescope $T_2$ formed in this way by the objective $O_2$ and the lens $L_2$ enables enlargement of the diameter of the beam $L_{Mes}$ by a factor of 6.06.

Thus at the entry of the objective $O_M$ of the microscope the diameter of the measurement beam $L_{Mes}$ is approximately 19 mm. In the example of operation of the microscope in a liquid medium in order in particular to observe organic molecules in solution, this beam width makes it possible to cover the entry pupil of the objective with an optimized luminous intensity distribution.

The objective $O_M$ of the microscope for operation in a liquid medium has a numerical aperture of 1.65. It is a special objective that requires the use of a microscope cover slip $G_S$ with a refractive index at 633 nm of n=1.78450, higher than that of standard optical glass.

To produce the coupling medium of the microscope, an immersion oil $H_i$ such as GEM refractometer liquid n (5893A)=1.81±0.005 immersion oil from Cargille Laboratories is preferably used in order to have the best possible match between the index of the cover slip $G_S$ and that of the immersion oil $H_i$.

A 45 nm metal layer $M_S$ is deposited on an external face of the cover slip $G_S$ to generate a surface plasmon at the interface of this metal layer with a dielectric observation medium D.

Given these conditions, the beam $L_{Mes}$ entering the objective $O_M$ is focused exactly at the interface between the metal layer $M_S$ covering the glass cover slip $G_S$ and the observation dielectric medium D, which here is a liquid.

After passing through the coupling medium, the light $L_{Mes}$ is reflected by the metal surface $M_S$ and passes through the objective $O_M$ in the opposite direction.

The position of the focusing point of the measurement laser beam $L_{Mes}$ relative to the gold layer $M_S$ being a parameter of fundamental importance for the contrast of the images obtained by the microscope, this position is controlled by means of a piezo-electric positioning device with a resolution of a few tens of nanometers over a range of 100 μm.

For this reason the axis of the objective $O_M$ is aligned with the normal to the surface of the plate $G_s$ by a positioning system (not shown in FIG. 6) providing four-axis manual control of the objective $O_M$ and two-axis manual control of the support of the cover slip $G_s$.

The objective and likewise the turntable are furthermore carried by two piezo-electrically driven turntables $PL_1$, $PL_2$ enabling accurate movement in two mutually-orthogonal directions X, Y in the same plane and a positioning accuracy better than 10 nm. These turntables $PL_1$, $PL_2$ are advantageously controlled by electronic control means EC connected to a control and command computer COMP.

The microscope of the invention also includes piezo-electric means for moving the objective $O_M$ in translation in a direction Z normal to the plane of each of the surfaces of the glass cover slip $G_S$ and the metal layer $M_S$ covering one of those surfaces.

If the alignment is correct, the beam reflected by the metal layer $M_S$ returns via the spatial filter $F_S$, the objective $O_2$, and the acoustical-optical modulator $AOM_{Mes}$ to be mixed with the reference beam $L_{Ref}$ in the beam splitter cube BS. The beam frequency is shifted by $2.O_{Mes}$ relative to the initial beam.

At the exit from the interferometer there is obtained a single light beam $L_V$ formed of the sum of the reference and measurement beams $L_{Ref}/L_{Mes}$ which beam passes through a diaphragm $D_2$ onto an optical detector such as a photodetector PD, for example. The optical signal V resulting from the detection of the beam $L_V$ is temporally modulated, producing the sum and difference of the optical frequencies of the two beams, i.e. $2O_{Mes}+2O_{Ref}$ and $2O_{Mes}-2O_{Ref}$. Because of the temporal response of the detector PD, only the component of the signal V whose frequency corresponds to the difference $2O_{Mes}-2O_{Ref}$ is used, of value that is 100 kHz in the chosen configuration.

The output signal V of the photodetector PD is filtered by an appropriate filter (not shown) and then demodulated by synchronous detection means $D_{Tec}$ that also receive the synchronous detection reference signal $V_{Ref}$ resulting from frequency mixing and filtering of the two modulating signals of the acoustical-optical modulators $AOM_{Ref}$ and $AOM_{Mes}$ by the mixer and the low-pass filter F. The demodulated signal $V_d$ is then sent for digital-analog conversion to the microcomputer COMP, which then forms the images.

The images are constructed point by point by scanning the position in a plane parallel to that of the cover slip $G_s$ relative to the objective $O_M$ by means of the turntables $PL_1$, $PL_2$.

The contrast of these images depends on the technique for defining profiles V(z) obtained by scanning in the direction Oz (normal to the cover slip $G_S$) and of variations that have a strong correlation with the surface plasmon.

Because the scanning is effected at a fixed position z it is possible to obtain images of the FIG. 4B type of particles with a size of a few tens of nanometers, for example a 50 nm diameter latex particle in FIG. 4, with a resolution of the order of 200 nm.

The microscope 1 of the invention also has the advantage of great versatility of use and configuration.

In particular, the microscope of the invention enables differential-mode high-resolution plasmon microscope imaging. To this end, the polarization converter CP is used to scan the sample to be observed linearly or alternately and synchronously with the turntables $PL_1$, $PL_2$ by beams polarized in pure p mode (radial polarization) and in pure s mode (azimuth polarization). This improves the contrast and the dynamic range of the images.

Another use of the optical signal obtained with the beams polarized in pure s mode is to slave the vertical position of the objective relative to the sample to be observed. Analyzing electrical signals established from reflected light beams polarized in s mode makes it possible to determine the absolute value of the position of the objective $O_M$ and, given this position, it is then possible to correct all mechanical and thermal drift inherent to a high-resolution microscope.

Such a technique for correcting the position of the objective of the microscope is not in itself totally novel in the field of microscopy, but the particular feature of the microscope of the invention is that it is the imaging system itself that makes it possible to make the correction and not an add-on system in parallel with the imaging system. Because of this, and without disturbing the optical plasmon measurement, the microscope is not made more complex in any way and its adjustment cost is not greatly increased. Moreover, such a facility for slaving the position of the objective $O_M$ relative to the observed sample makes it possible to achieve greater accuracy in measuring the intensity of the function V(z).

Another advantage of the microscope of the present invention is that it makes it possible to construct images in three dimensions of the measured function V(z). The construction of such three-dimensional "maps" of the function V(z) makes it possible to find the optical section plane yielding the best image contrast. To this end, these 3D images undergo post-processing and the plane Z of optimum contrast is then determined by interpolation.

The invention claimed is:

1. A high-resolution scanning surface-plasmon microscope including:
    a source (LG) of coherent light;
    a medium for coupling and confining a surface plasmon including an objective (O, $O_M$) with a large numerical aperture, immersion oil ($H_i$), and a glass cover slip ($G_s$);
    a metal layer ($M_s$) covering a surface of the glass cover slip ($G_s$) of the coupling medium that is not in contact with the immersion oil thereof, the metal layer being adapted to be brought into contact with an observation medium (D) containing a sample to be observed and to emit a surface plasmon generated by excitation of at least one light beam (L) coming from the light source (LG);
    a heterodyne-mode Twyman-Green interferometer adapted to split a light beam emitted by the light source into at least one reference beam ($L_{Ref}$) and at least one measurement beam ($L_{Mes}$) directed toward the coupling medium and the metal layer ($M_s$) to generate a surface plasmon, the interferometer being positioned between the light source and the objective of the coupling medium to form an interferometric beam ($L_v$) between a reference beam and a measurement beam after reflection of each of them by a mirror (M) and by the metal layer ($M_s$), respectively;

at least one beam enlarger (BE) placed between the light source (LG) and the interferometer and between the interferometer and the coupling medium (O, $O_M$, $H_i$, $M_s$);

means ($PL_1$, $PL_2$, EC) for scanning the metal layer with the measurement light beam, including piezoelectric means ($PL_1$, $PL_2$) for relative movement in translation between the cover slip ($G_S$) and the objective (O, $O_M$) of the coupling medium in two mutually-orthogonal directions X, Y in the same plane and piezoelectric means for moving the objective (O, $O_M$) in translation in a direction Z normal to the plane of each of the surfaces of the glass cover slip ($G_s$) and the metal layer ($M_s$) covering one of them;

means (PD) for detecting the interferometric beam from the interferometer; and processing means (S, F, $D_{Tec}$, COMP) for forming an image from the interferometric beam and being disposed between the light source and the interferometer, at least one polarization converter (CP) for converting the light beams (L) emitted by the light source (LG) from linear polarization to radial polarization in pure p mode in which all the electric field vectors $E_0$ relative to the propagation axis of the beam L are all oriented radially relative to the propagation axis and from the linear polarization to azimuth polarization in pure s mode in which all the electric field vectors $E_0$ relative to the propagation axis of the beam L are all oriented in azimuth direction relative to the propagation axis, thereby enabling detection of dielectric or metal objects with a diameter less than 10 nm without marking, the piezoelectric means ($PL_1$, $PL_2$, EC) for scanning the metal layer alternately with beams polarized in radial polarization in pure p mode and in azimuth polarization in pure s mode.

2. A microscope according to claim 1, characterized in that a first or reference arm of the interferometer includes a mirror ($M_{Ref}$) for reflecting the reference light beam ($L_{Ref}$) and a second or measurement arm in which the measurement beam ($L_{Mes}$) propagates includes the coupling medium (O, $O_M$, $H_i$, $M_S$) and the metal layer ($M_S$) covering a surface of the glass cover slip ($G_s$) thereof.

3. A microscope according to claim 1, characterized in that each arm of the interferometer includes at least one acoustical-optical modulator ($AOM_{Ref}$, $AOM_{Mes}$) adapted to shift the optical frequency of the reference light beam ($L_{Ref}$) and the measurement beam ($L_{Mes}$), respectively.

4. A microscope according to claim 1, characterized in that the means (PD) for detecting the interferometric beam ($L_v$) include at least one of the following elements: photomultiplier, CCD camera, photon counter, avalanche photodiode.

5. A microscope according to claim 1, characterized in that the observation medium (D) is a dielectric medium of refractive index that is less than 1.5.

6. A microscope according to claim 1, characterized in that the objective (O, $O_M$) of the coupling medium has a numerical aperture greater than or equal to 1.2 in air and 1.55 in an aqueous solution and a magnification of greater than 60 times.

7. A microscope according to claim 1, characterized in that the source (LG) of coherent light is a laser and notably a helium-neon (He—Ne) gas laser.

8. A heterodyne interferometer high-resolution surface-plasmon microscopy method, comprising the steps of:

using a measurement light beam ($L_{Mes}$) produced by a coherent light beam (LG) introduced into a heterodyne-mode Twyman-Green interferometer to illuminate a sample to be imaged that is disposed on a metal layer ($M_S$) coating a glass cover slip ($G_S$) of a medium for coupling and confining a surface plasmon also including an objective (O, $O_M$) with a large numerical aperture and immersion oil ($H_i$); at least one beam enlarger (BE) placed between the light source (LG) and the interferometer and between the interferometer and the coupling medium (O, $O_M$, $H_i$, $M_S$);

scanning the surface of the metal layer with the measurement beam guided by scanning means ($PL_1$, $PL_2$, EC), including piezoelectric means ($PL_1$, $PL_2$) for relative movement in translation between the cover slip ($G_S$) and the objective (O, $O_M$) of the coupling medium in two mutually-orthogonal directions X, Y in the same plane and piezoelectric means for moving the objective (O, $O_M$) in translation in a direction Z normal to the plane of each of the surfaces of the glass cover slip ($G_S$) and the metal layer ($M_S$) covering one of them;

detecting an interferometric light beam at the exit from said Twyman-Green interferometer by detection means (PD);

processing said interferometric beam and forming an image of the surface plasmon emitted by the metal surface in contact with the sample to be imaged by processing and image-forming means (S, F, $D_{Tec}$, COMP);

characterized in that the beam (LG) of coherent light is alternately polarized by the polarization converter (CP) in pure p mode in which all the electric field vectors $E_0$ relative to the propagation axis of the beam L are al oriented radially relative to the propagation axis and in pure s mode in which all the electric field vectors $E_0$ relative to the propagation axis of the beam L are all oriented in azimuth direction relative to the propagation axis and the surface of the metal layer is scanned by the piezoelectric means ($PL_1$, $PL_2$) linearly, alternately and synchronously with the alternating polarization of the beam of coherent light by the measurement beam ($L_{MES}$) polarized alternately in pure p mode and in pure s mode for differential mode imaging of the sample positioned on the metal layer of the coupling medium.

* * * * *

UNITED STATES PATENT AND TRADEMARK OFFICE
CERTIFICATE OF CORRECTION

PATENT NO. : 8,610,897 B2  Page 1 of 1
APPLICATION NO. : 12/747266
DATED : December 17, 2013
INVENTOR(S) : Berguiga et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 615 days.

Signed and Sealed this
Twenty-second Day of September, 2015

Michelle K. Lee
*Director of the United States Patent and Trademark Office*